US010386292B2

(12) United States Patent
Nohmi et al.

(10) Patent No.: US 10,386,292 B2
(45) Date of Patent: Aug. 20, 2019

(54) EROSION PREDICTION METHOD, EROSION PREDICTION SYSTEM, EROSION CHARACTERISTICS DATABASE USED IN THIS PREDICTION, AND METHOD FOR CONSTRUCTING THE SAME

(71) Applicant: EBARA CORPORATION, Tokyo (JP)

(72) Inventors: Motohiko Nohmi, Tokyo (JP); Hiroshi Yakuwa, Tokyo (JP); Keisuke Hayabusa, Tokyo (JP); Hiroaki Nakamoto, Tokyo (JP)

(73) Assignee: EBARA CORPORATION, Tokyo (JP)

( * ) Notice: Subject to any disclaimer, the term of this patent is extended or adjusted under 35 U.S.C. 154(b) by 743 days.

(21) Appl. No.: 14/403,830

(22) PCT Filed: May 31, 2013

(86) PCT No.: PCT/JP2013/065180
§ 371 (c)(1),
(2) Date: Nov. 25, 2014

(87) PCT Pub. No.: WO2013/180264
PCT Pub. Date: Dec. 5, 2013

(65) Prior Publication Data
US 2015/0135809 A1 May 21, 2015

(30) Foreign Application Priority Data

Jun. 1, 2012 (JP) .................................. 2012-126217

(51) Int. Cl.
*G01N 17/00* (2006.01)
*F04D 15/00* (2006.01)
(Continued)

(52) U.S. Cl.
CPC .......... *G01N 17/00* (2013.01); *F04D 15/0088* (2013.01); *F04D 29/669* (2013.01);
(Continued)

(58) Field of Classification Search
CPC .. G06F 19/00; G06F 17/5018; G06F 2217/76; G01N 17/00; G01N 3/567;
(Continued)

(56) References Cited

U.S. PATENT DOCUMENTS 4,058,004 A * 11/1977 Hammitt ................ G01N 3/567
73/590
2004/0244382 A1* 12/2004 Hagen ................... F01K 21/047
60/775
(Continued)

FOREIGN PATENT DOCUMENTS

| JP | H11-37979 A | 2/1999 |
|----|-------------|--------|
| JP | 2007-327455 A | 12/2007 |

(Continued)

OTHER PUBLICATIONS

Dular et al., "Numerical modelling of cavitation erosion", Intl. J. Numerical Methods in Fluids 61 (2009).*
(Continued)

*Primary Examiner* — Mohamed Charioui
*Assistant Examiner* — Catherine T. Rastovski
(74) *Attorney, Agent, or Firm* — Pearne & Gordon LLP

(57) ABSTRACT

To provide an erosion characteristics database and a method for constructing the same, an erosion prediction method and an erosion prediction system using the database for predicting a widespread erosion amount of a fluid machine or the like in a short time without the need for an operation of a model machine or an actual machine.

A method for predicting erosion of a fluid machine surface due to cavitation, the method including: calculating erosion intensity distribution in each area of the fluid machine surface from cavitation flow field characteristics obtained using cavitation CFD in a flow path formed by the fluid machine; determining radius distribution and center position (Continued)

distribution of a representative sphere and the number of shape deformations by the representative sphere for assuming an erosion surface having a porous surface property based on the erosion intensity distribution; determining a fluid machine surface to be predicted as an approximate erosion surface; and calculating a shape after deformation of the approximate erosion surface based on the radius distribution and the center position of the representative sphere and the number of shape deformations by the representative sphere.

14 Claims, 10 Drawing Sheets

(51) Int. Cl.
    *F04D 29/66*     (2006.01)
    *G01N 3/56*     (2006.01)
    *G06F 17/50*     (2006.01)

(52) U.S. Cl.
    CPC .......... *G01N 3/567* (2013.01); *G06F 17/5018* (2013.01); *F05D 2260/81* (2013.01); *F05D 2260/821* (2013.01); *G06F 2217/76* (2013.01)

(58) Field of Classification Search
    CPC .............. G04D 15/0088; F04D 29/669; F05D 2260/81; F05D 2260/821
    USPC ................. 702/34, 50, 98, 100, 136; 60/775
    See application file for complete search history.

(56) References Cited

U.S. PATENT DOCUMENTS

| | | | |
|---|---|---|---|
| 2007/0213944 A1 | 9/2007 | Matsuzawa et al. | |
| 2008/0215255 A1* | 9/2008 | Stockner | G06F 17/5018 702/34 |
| 2010/0324836 A1* | 12/2010 | Ramachandran | G01N 17/006 702/35 |
| 2012/0118395 A1* | 5/2012 | Wang | F17D 1/08 137/13 |

FOREIGN PATENT DOCUMENTS

| | | |
|---|---|---|
| JP | 2008-198161 A | 8/2008 |
| JP | 2009-209792 A | 9/2009 |
| JP | 2010-101192 A | 5/2010 |
| JP | 2011-157894 A | 8/2011 |

OTHER PUBLICATIONS

Fortes-Patella et al., Cavitation erosion mechanism: numerical simulations of the interaction between pressure waves and solid boundaries, CAV 2001, Proceedings of the Fourth International Symposium on Cavitation, California Institute of Technology, Pasadena, CA, USA, Jun. 20-23, 2001.*

Zhang X, Morris J, Klette, R "Volume measurement using a laser scanner," Communication, and Information Technology Research (CITR) Computer Science Department, The University of Auckland (2005).*

Nohmi M. An Approximation Method for the Cavitation Eroded Surface. ASME. Fluids Engineering Division Summer Meeting, vol. 2, Fora: Cavitation and Multiphase Flow; Fluid Measurements and Instrumentation; Microfluidics; Multiphase Flows: Work in Progress (2013).*

K.Y. Chiu et al., "Evolution of Surface roughness of some metallic materials in cavitation erosion", Ultrasonics 43 (2005).*

International Search Report for Application No. PCT/JP2013/065180 dated Aug. 27, 2013.

European Search Report dated Jan. 15, 2016 for Application No. EP13796355.

Chiu, et al. "Evolution of surface roughness of some metallic materials in cavitation erosion." Ultrasonics, IPC Science and Technology Press Ltd., Guildford, GB, vol. 43, No. 9, Oct. 1, 2005, p. 713-716.

Dular, et al. "Numerical modelling of cavitation erosion." International Journal for Numerical Methods in Fluids, vol. 61, No. 12, Dec. 30, 2009, p. 1388-1410.

Hideyuki Tanaka, "Development of a Numerical Procedure to Predict the Flowfied with Sand Erosion", The Japan Society of Mechanical Engineers, dated Oct. 1997.

* cited by examiner

*Figure 2*

| | MATERIAL NAME | TENSILE STRENGTH | HARDNESS | CAVITATION INTENSITY | TEST TIME (Hrs) | EROSION VOLUME | AVERAGE EROSION DEPTH |
|---|---|---|---|---|---|---|---|
| 1 | A | 100 | 800 | 1 | 1 | | |
| 2 | A | 100 | 800 | 1 | 10 | | |
| 3 | A | 100 | 800 | 1 | 100 | | |
| 4 | A | 100 | 800 | 2 | 1 | | |
| 5 | A | 100 | 800 | 2 | 10 | | |
| 6 | A | 100 | 800 | 2 | 100 | | |
| 7 | A | 100 | 800 | 3 | 1 | | |
| 8 | A | 100 | 800 | 3 | 10 | | |
| 9 | A | 100 | 800 | 3 | 100 | | |
| 10 | B | 200 | 1000 | 1 | 1 | | |
| 11 | B | 200 | 1000 | 1 | 10 | | |
| 12 | B | 200 | 1000 | 1 | 100 | | |
| 13 | B | 200 | 1000 | 2 | 1 | | |
| 14 | B | 200 | 1000 | 2 | 10 | | |
| 15 | B | 200 | 1000 | 2 | 100 | | |
| 16 | B | 200 | 1000 | 3 | 1 | | |
| 17 | B | 200 | 1000 | 3 | 10 | | |
| 18 | B | 200 | 1000 | 3 | 100 | | |
| 19 | C | 300 | 600 | 1 | 1 | | |
| 20 | C | 100 | 600 | 1 | 10 | | |
| 21 | C | 100 | 600 | 1 | 100 | | |
| . | . | . | . | . | . | . | . |
| . | . | . | . | . | . | . | . |

Figure 6
(A) 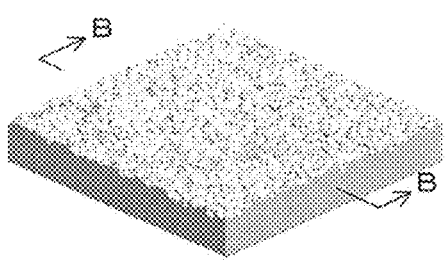
AFTER TRIAL OF 6000 TIMES
(B) 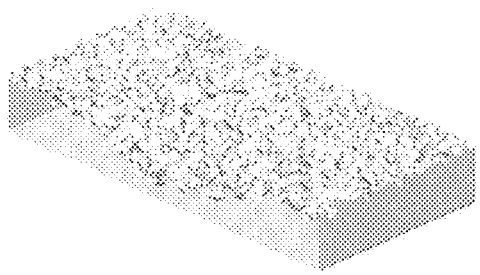
SECTION AFTER TRIAL
OF 6000 TIMES

Figure 9
(A)
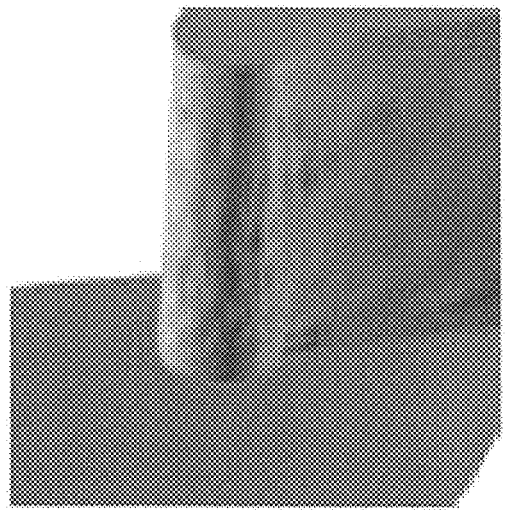
(B)
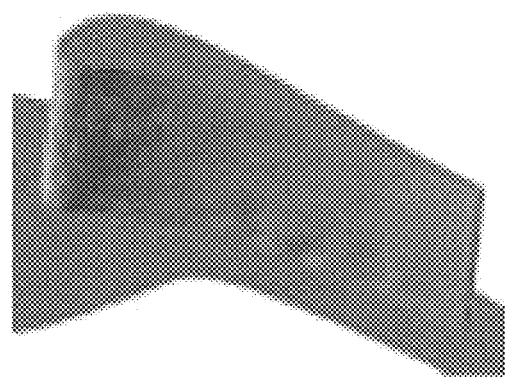
(C)
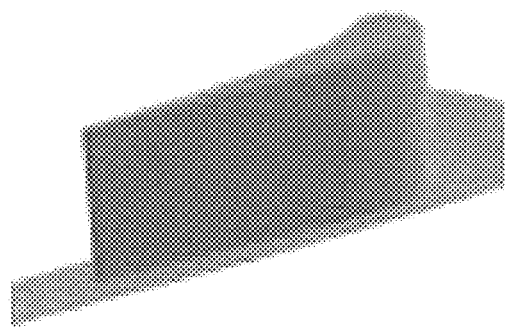

Figure 10
(A)
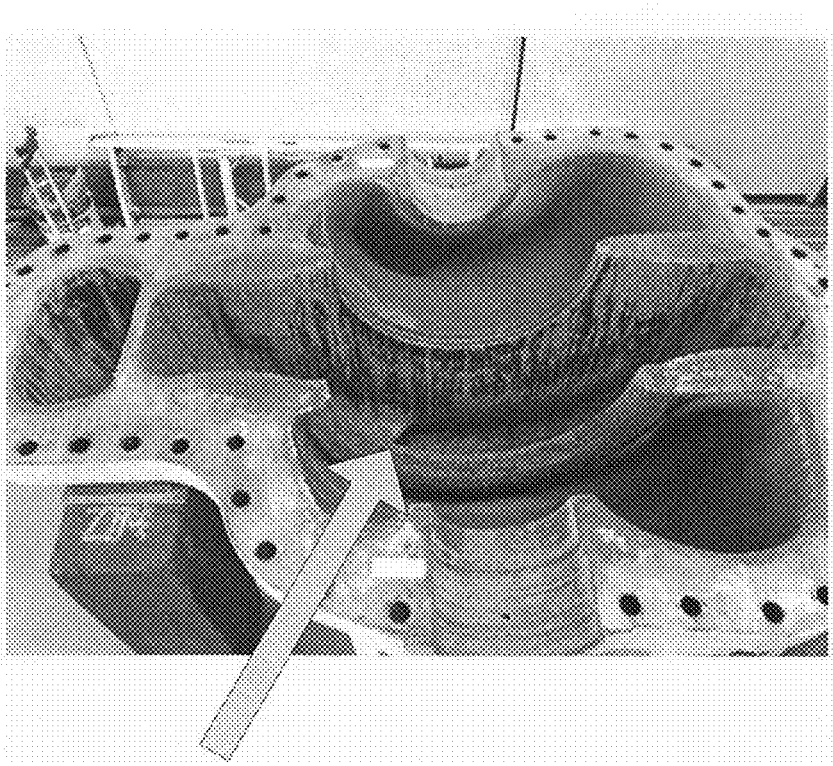
(B)
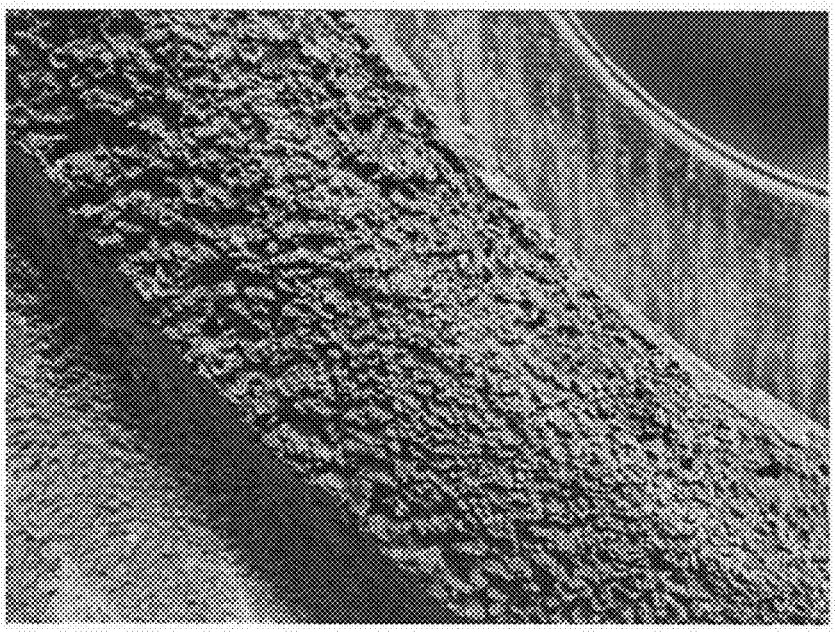

EROSION PREDICTION METHOD, EROSION PREDICTION SYSTEM, EROSION CHARACTERISTICS DATABASE USED IN THIS PREDICTION, AND METHOD FOR CONSTRUCTING THE SAME

TECHNICAL FIELD

The present invention relates to an erosion prediction method, an erosion prediction system, an erosion characteristics database used in this prediction, and a method for constructing the same, and more particularly to an erosion prediction method, an erosion prediction system, an erosion characteristics database used in this prediction, and a method for constructing the same for predicting in a short time, cavitation erosion produced in a fluid machine, a pipe, or other structures in a fluid.

BACKGROUND ART

Surfaces of a fluid machine, a pipe, or other structures in a fluid are damaged by various phenomena such as cavitation erosion or corrosion, or solid particle impact. This prevents desired fluid performance from being maintained or reduces strength of the structures. For such phenomena, establishing a technique of predicting development of damage is a major challenge. This application particularly notes prediction of cavitation erosion.

Cavitation erosion is a phenomenon such that cavitation occurs in a low pressure portion in a flow path of a fluid machine or the like, and when this disappears in the downstream, impulsive pressure is generated to erode a surface of the fluid machine or the like. Since the development of the cavitation erosion reduces strength of a structure such as a fluid machine or efficiency of the fluid machine as described above, prediction of the cavitation erosion is extremely significant. For the cavitation erosion, prediction of risk of surface erosion in a stage without any deformation based on CFD (computational fluid dynamics), and construction of a theoretical model of damage in a relatively minute scale of a material surface have been partly proposed. FIG. 10 shows a photograph of a pump casing with actually developing erosion, FIG. 10(A) shows the entire pump casing, and FIG. 10(B) shows a portion with significantly developing erosion shown by the arrow in FIG. 10(A).

As a related technique disclosing a method for predicting an amount of erosion due to cavitation, a technique using soft metal is proposed (see Patent Document 1).

The prediction method includes:
1) predicting a generation position of cavitation erosion in a model fluid machine or an actual fluid machine,
2) forming the generation position by using a soft metal,
3) operating the fluid machine to cause erosion on a surface of the soft metal,
4) measuring an amount of deformation due to the erosion using measurement means,
5) calculating, based on the deformation amount, a deformation speed that is a time change of the deformation amount,
6) calculating cavitation intensity using a database on a relationship between the deformation speed and the cavitation intensity, and
7) predicting the amount of erosion due to cavitation based on the cavitation intensity.

Also, using vibration or noise as an index of an erosion amount or an erosion risk has been also proposed. (see Patent Document 2).

Patent Document 1: JP-A-2007-327455
Patent Document 2: JP-A-H11-37979

SUMMARY OF THE INVENTION

Technical Problem

However, the inventions according to the above related techniques have various problems as described below. 1) The pump needs to be actually fabricated, 2) if removal of paint is an index, an experiment needs to be conducted again for each change of an operation condition, 3) when soft metal is attached, there may be an influence of an attachment way such as a double-sided tape, 4) when cavitation erosion develops, pump performance changes, but an influence thereof is not considered, or the like.

The present invention is achieved in view of the above described various problems, and has an object to provide an erosion characteristics database, a method for constructing the same, an erosion prediction method and an erosion prediction system using the database for predicting a widespread erosion amount of a structure such as a fluid machine in a short time without the need for an operation of a model machine or an actual machine.

Solution to Problem

To achieve the object, the present invention provides a method for predicting erosion of a fluid machine produced due to cavitation, the method including: calculating erosion intensity distribution in each area of the fluid machine from cavitation flow field characteristics obtained using cavitation CFD for a flow path formed by the fluid machine; calculating a surface after erosion of the fluid machine as an approximate erosion surface based on the erosion intensity distribution; recalculating erosion intensity distribution in each area of the fluid machine using the cavitation CFD for a flow path including the calculated approximate erosion surface; and recalculating a shape after deformation of the approximate erosion surface based on the recalculated erosion intensity distribution.

Also, the calculating the approximate erosion surface includes: approximating the surface as an aggregate of multiple spherical surfaces for assuming an erosion surface having a porous surface property particularly remarkably observed in a metal material based on the erosion intensity distribution; determining radius distribution and center position distribution of a representative sphere of the spherical surfaces (hereinafter referred to as a representative sphere), and the number of shape deformations by the representative sphere; and calculating a shape after deformation of the approximate erosion surface based on the determined information on the representative sphere.

The method further includes: calculating erosion depth distribution produced in the fluid machine surface based on the erosion intensity distribution: and calculating the shape after deformation of the approximate erosion surface by the spherical surface also using the erosion depth distribution.

The method includes: prior to the calculation of the erosion intensity distribution, calculating the erosion intensity distribution in each area for an initial shape of the fluid machine without erosion from the cavitation flow field characteristics obtained using the cavitation CFD; changing surface roughness in each area of the fluid machine surface for assuming minute deformation action in an incubation period in an early stage of erosion based on the erosion intensity distribution; calculating erosion intensity distribution for the initial shape again by the cavitation CFD; and predicting erosion based on the calculated erosion intensity distribution.

The method further includes: prior to the calculation of the erosion intensity distribution, measuring the shape of the fluid machine in which erosion has been already produced by an actual operation; calculating, based on the measurement result, erosion intensity distribution for the shape including erosion of the fluid machine using the cavitation CFD for a flow path including the erosion surface that has been already produced; and predicting erosion based on the calculated erosion intensity distribution.

Also, an erosion prediction system for performing the erosion prediction method is provided including: a computer having storage means and a CPU; input means for inputting information in the computer; and display means for displaying a result calculated by the computer, wherein the storage means stores an erosion prediction program for performing the erosion prediction method, the CPU reads the erosion prediction program from the storage means, calculates a predicted shape of a fluid machine after erosion based on shape data and material information of the fluid machine input by the input means, and displays information on the predicted shape on the display means.

The CPU calculates a shape change of the fluid machine over time, and displays the shape change on the display means by animation.

Also, a database on erosion characteristics of materials used for a fluid machine is provided including information on material names, material properties, and erosion characteristics for predetermined erosion intensity, wherein the erosion characteristics include an erosion volume, an erosion depth, erosion depth distribution, and a surface property of an erosion surface, and the surface property is surface roughness or a surface shape pattern of the fluid machine.

The information on the erosion characteristics includes at least two sets of information at different times over time.

The information in the erosion characteristics database according to claim 8 or 9 is used in performing the cavitation CFD.

Further, the storage means stores information in the erosion characteristics database according to claim 8 or 9, and the information in the database is used for erosion prediction.

BRIEF DESCRIPTION OF DRAWINGS

FIG. 2 shows an example of an erosion characteristics database.

FIG. 5(A) shows an initial shape, FIGS. 5(B) to 5(G) show approximate erosion surfaces at the numbers of trials of 1000, 2000, 3000, 4000, 5000, and 6000, and FIG. 5(H) is a sectional view taken along the line H-H in FIG. 5(G).

FIG. 6 shows a situation in which an entire upper surface of a rectangular parallelepiped solid model including an initial indentation created by rotating a sine curve is hollowed 6000 times by a representative sphere having the same radius, FIG. 6(A) is an overall perspective view, and FIG. 6(B) is a sectional view taken along the line B-B in FIG. 6(A).

FIG. 7(A) shows an initial shape, FIGS. 7(B) to 7(G) show approximate erosion surfaces at the numbers of trials of 1000, 2000, 3000, 4000, 5000, and 6000, and FIG. 7(H) is a perspective view from a different point of view from that in FIG. 7(G).

FIG. 8(A) shows an initial shape, FIGS. 8(B) to 8(G) show approximate erosion surfaces at the numbers of trials of 1000, 2000, 3000, 8000, 9000, 10000.

FIG. 9 shows results of damage to a surface of a fluid machine (turbine blade surface) due to sand particles obtained by a coupled analysis of a fluid side and a material side, FIG. 9(A) shows a vicinity of a front edge, FIG. 9(B) shows a positive pressure surface, and FIG. 9(C) shows a negative pressure surface.

FIG. 10 is a photograph showing a fluid machine with developing erosion, FIG. 10(A) shows the entire pump casing, and FIG. 10(B) is an enlarged photograph showing a surface near an arrow in FIG. 10(A).

DESCRIPTION OF EMBODIMENTS

Figure 1:
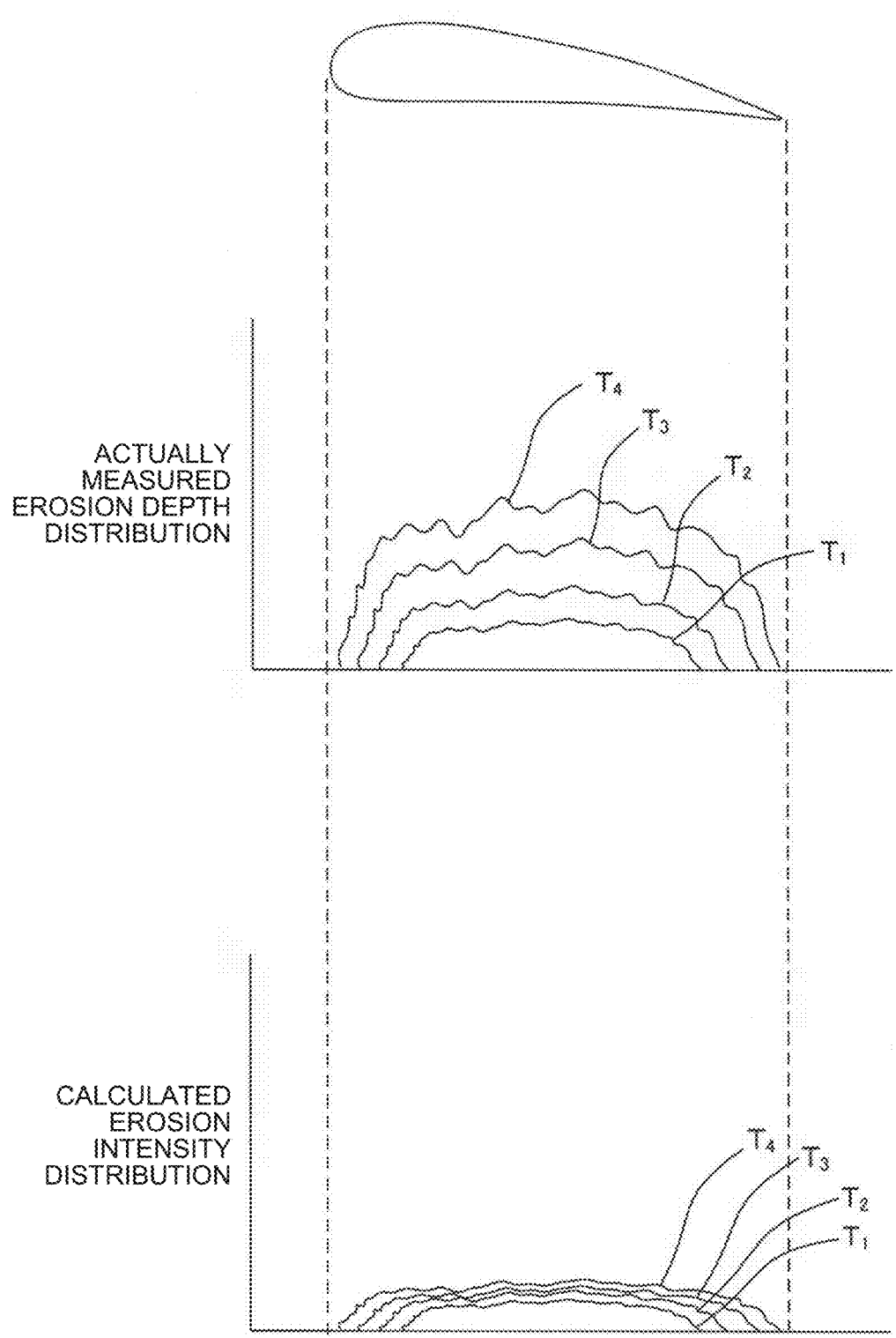
FIG. 1 shows correlation between actually measured erosion depth distribution and calculated erosion intensity distribution.

The present invention includes analyzing erosion due to cavitation using CFD as one feature. To this end, cavitation, erosion, and CFD will be first outlined.

Cavitation is a phenomenon in which when pressure in a liquid flow is lower than saturated vapor pressure, a liquid boils with extremely minute bubble nuclei in the liquid, or multiple small bubbles are formed by isolation of a dissolved gas. The cavitation causes erosion as noted by this application, or reduces a thrust force when occurring in a ship screw.

Next, erosion is a phenomenon such that collapse of bubbles generated by the cavitation described above damages a surface of a structure. The collapse of the cavitation generates an impact force of several hundred MPa or more or a microjet. Thus, if bubbles collapse near a surface of the structure, the impact force or the microjet deforms a wall surface of the structure or chips a material of the structure from the surface. Further development of erosion causes perforation of the structure, or drop of a part of the structure. Thus, erosion is a significant problem for fluid machines.

Further, the CFD refers to computational fluid dynamics, which is a numerical analysis and prediction method for observing a flow by solving an equation on fluid motion using a computer. A procedure for calculation includes the steps of 1) model data creation, 2) grid generation, and 3) analysis. Specifically, in the model data creation step, a 3D or 2D model that is reproduction of a shape of a target object is created. CAD is used for design, and CAD data is often used. For the grid generation step, the computational fluid dynamics discretely deals with space, and thus an object shape and space around the object need to be discretized, and generally expressed by a grid (or mesh). The grid generation includes various methods such as an unstructured grid method using a tetrahedron, or an orthogonal grid method using a rectangular parallelepiped. In the analysis step, an approximate solution of a flow equation for each grid is calculated using a computer. The calculation provides pressure, a flow velocity, density or the like of each grid.

Next, an erosion characteristics database and a method for constructing the same, an erosion prediction method and an erosion prediction system using the database according to an embodiment of the present invention will be described.

[Construction of Erosion Characteristics Database]

Prior to erosion prediction, an erosion characteristics database on various materials needs to be constructed. This is because even with the same cavitation intensity, erosion characteristics differ depending on materials of a structure.

To check a relationship between materials and erosion characteristics, a magnetostrictive test and a jet test are standardized. The magnetostrictive test is conducted by placing a test piece in a fluid, and applying ultrasonic vibration to the test piece to cause cavitation in a surface of the test piece. After a lapse of a predetermine operation time, a change in the test piece is measured to check erosion characteristics of the material. In some cases, the test piece is not vibrated, but bubbles are generated on the test piece by an ultrasonic vibrator placed to face the test piece, and the bubbles cause erosion in the test piece.

There is also a test using a cavitation jet. This test is performed by issuing a fast submerged water jet to cause cavitation around the jet. This allows a test in consideration of a flow velocity of a fluid, static pressure, or cavitation coefficient. Further, there is a test method using a venturi tube. This is performed by passing a fluid in the venturi tube at high speed to cause cavitation, and placing a test piece in a cavitation produced area. Like the test using a jet, this allows a test in consideration of cavitation coefficient, a flow velocity, static pressure or the like. Besides, a test method of placing a test piece on a blade surface of a hydrofoil placed in a flow path, and causing erosion in the test piece by cavitation produced on the hydrofoil, or a test method of fabricating a pump, a water wheel, or a screw propeller like an actual machine and placing a test piece on a surface thereof, or causing erosion in the surface of the pump, the water wheel, or the propeller can be performed.

The tests as described above cause erosion in the surface of the test piece, and cavitation intensity and a time change of the test piece are precisely measured, thereby constructing the database. Specifically, various reference erosion production devices as described above are used to obtain correlation data between cavitation intensity and erosion by cavitation CFD for each significant material. As data on erosion characteristics, an erosion volume and an average erosion depth for each significant material, and also erosion depth distribution and surface properties of an erosion surface (surface roughness or a surface shape pattern), and further data on lapses of time thereof are obtained (an erosion test is interrupted multiple times, and an erosion shape is obtained at each interruption). The shape is preferably measured using a 3D laser scanner or an impression material. For the cavitation CFD, an analysis in consideration of shape changes due to erosion is conducted multiple times (correspondingly to the times to obtain the erosion data) with development of erosion in the surface. Assuming that the changes (differences) in the erosion surface shape data obtained multiple times and cavitation erosion intensity obtained by calculation for each time correspond to each other, the database is constructed. Any of the test methods described above may be used, but in consideration of easiness to perform existing cavitation CFD, a venturi tube, a hydrofoil, or a pump, a water wheel, or a screw propeller similar to an actual machine is desirably applied.

The database is sorted into cavitation erosion intensity distribution and erosion development speed distribution by calculation, and change distribution of a surface property. Specifically, for each material, erosion intensity and an erosion development speed (a speed almost perpendicular to the erosion surface is taken) by the cavitation CFD are defined by approximate functions. The surface property is compiled into a three-dimensional database. A phenomenon of an increase in minute indentations referred to as pits which do not reduce the volume is well known in an incubation period. The number density and shape of the pits are also desirably compiled into a database. Changes in surface roughness are thereby desirably compiled into a database.

FIG. 1 shows an example of a hydrofoil, and shows a correlation between an actually measured erosion surface shape and calculated erosion intensity distribution. FIG. 1 shows graphs of erosion surface shapes in each area at times $T_1$ to $T_4$, and erosion intensity distribution calculated by CFD of a hydrofoil shape in consideration of deformation due to erosion at the times $T_1$ to T4. The erosion surface shape is taken as a combination of local average erosion depth distribution of a surface and a local property (three-dimensional roughness distribution of a porous surface), and a local difference in erosion depth distribution divided by an elapsed time is defined as an erosion development speed. This is associated with erosion intensity distribution at each time. As a difference method, any calculation method such as forward difference or central difference may be selected. Any association may be used, but approximation with a polynomial and determination of a coefficient by a least square method is easy. As an example, a simple forward difference will be described. It is considered that development of erosion between the times $T_1$ and $T_2$ corresponds to erosion intensity distribution calculated for the shape at the time $T_1$, erosion depth distribution at the time $T_1$ is subtracted from erosion depth distribution at the time $T_2$, and erosion depth distribution of the difference is divided by $\Delta T_{21}=T_2-T_1$. If curves of the erosion speed distribution and the erosion intensity distribution shape match well, for example, a linear function can be assumed to calculate a proportionality coefficient thereof. Similarly, it is considered that development of erosion between the times $T_2$ and $T_3$ corresponds to erosion intensity distribution calculated for the shape at the time $T_2$, erosion depth distribution at the time $T_2$ is subtracted from erosion depth distribution at the time $T_3$, and erosion depth distribution of the difference is divided by $\Delta T_{32}=T_3-T_2$. This is associated with the erosion intensity distribution for the shape at the time $T_2$. Further, it is considered that development of erosion between the times $T_3$ and $T_4$ corresponds to erosion intensity distribution calculated for the shape at the time $T_3$, and hereafter, association for any number of steps is repeated. The multiple times of association allows accurate calculation of an approximate function for calculating an erosion speed from the erosion intensity distribution as an input. Along therewith, relationships between the calculated erosion intensity, the erosion depth distribution, a fluid condition, a material condition, or the like and a local property of the erosion surface are compiled into a database. Thus, for a developing erosion surface, changes in the erosion depth and surface property can be predicted by calculation.

FIG. 2 shows an example of an erosion characteristics database on various materials. In construction of the database, there is no need to conduct tests for all available materials. This is because, based on properties (for example, tensile strength or hardness) of the materials, erosion characteristics of materials having close values of tensile strength or hardness can be estimated from data on tested materials with a certain level of accuracy. Also, erosion characteristics can be estimated from existing erosion data obtained by a magnetostrictive test device or a jet test device, and a relative comparison in resistance to cavitation erosion between the materials based on the erosion data.

Figure 3:
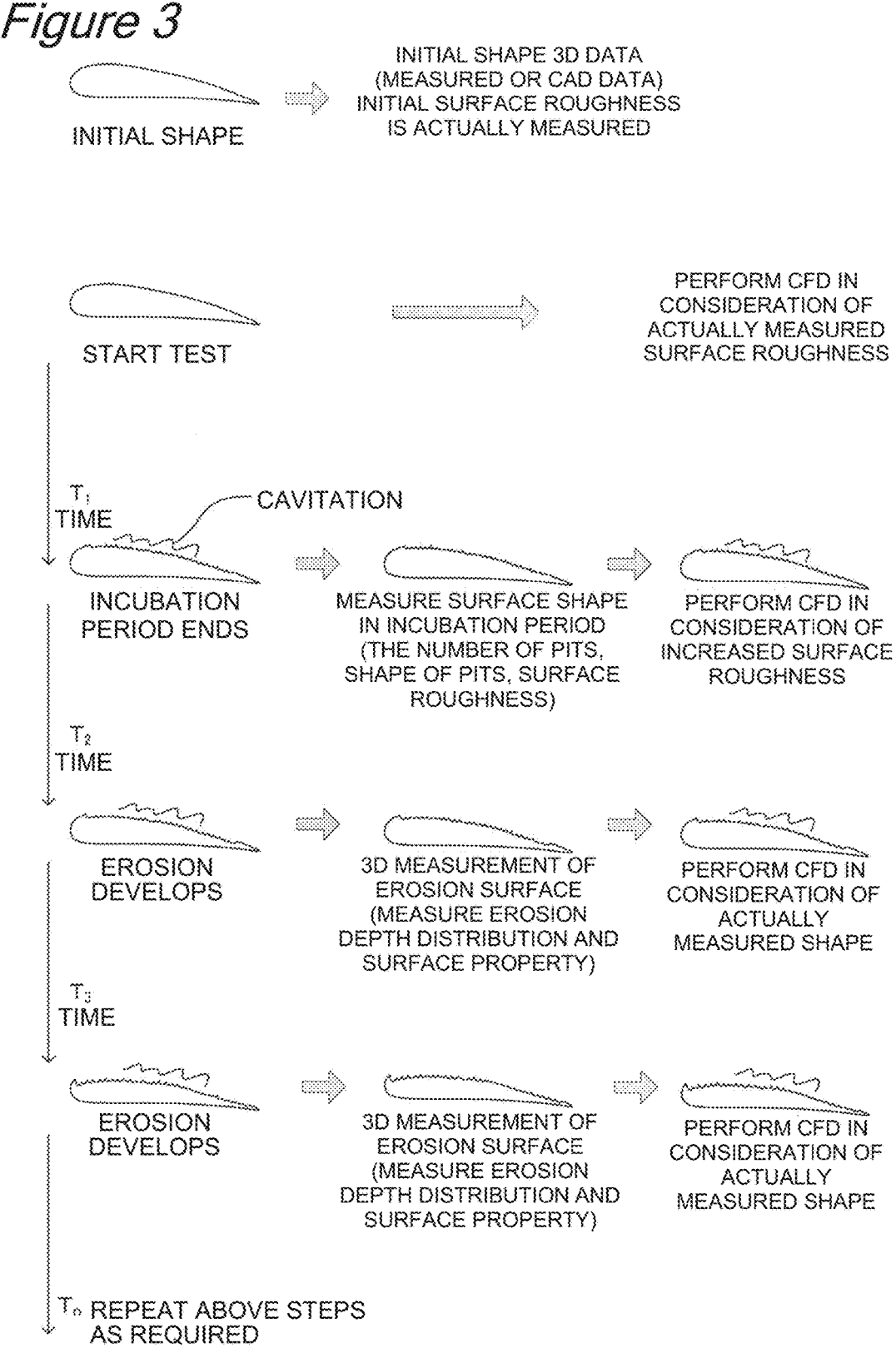
FIG. 3 shows a procedure for constructing an erosion characteristics database.

FIG. 3 is a conceptual view illustrating stages for constructing the erosion characteristics database. An erosion test for a certain material by a reference cavitation production device using an actual hydrofoil is herein described. First, an initial shape of a test object is obtained using three-dimensional (3D) CAD data, actually measured data, or the like. A surface property is actually measured.

Next, cavitation is actually produced by the cavitation production device, and the test object is placed in a cavitation produced area. Thus, a test for constructing a database is started. At this time, surface roughness has an influence on erosion characteristics. Thus, CFD is performed in consideration of actually measured surface roughness. Thus, erosion intensity distribution between the start of the test and the end of an incubation period (T=a lapse of $T_1$) is calculated.

The test is once stopped at the end of the incubation period to measure a surface shape of the test object. The number of pits, a shape of pits, surface roughness distribution, or the like are measured. Then, CFD is performed in consideration of the obtained surface shape. Thus, erosion intensity distribution between the end of the incubation period and an erosion period is calculated. At this time, erosion intensity distribution closer to an actual erosion phenomenon can be calculated because of consideration of the surface shape.

Then, the test object is again placed on the cavitation production device to produce cavitation. After the lapse of the incubation period, erosion is produced in the surface of the test object. Then, the test is stopped at the lapse of $T=T_2$ from the start of the test. A 3D shape (erosion depth distribution or a surface property) of the erosion surface is actually measured. Then, CFD is performed in consideration of the obtained surface shape. At this time, erosion intensity distribution closer to an actual erosion phenomenon can be calculated because of consideration of the shape of the test object deformed by erosion.

Further, the test object is again placed on the cavitation production device to produce cavitation. Then, the test is stopped at the lapse of $T=T_3$ from the start of the test, and a 3D shape (erosion depth distribution or surface property) of the erosion surface is actually measured. Then, CFD is performed in consideration of the obtained surface shape.

The above described steps of actual measurement and CFD are repeated several times as required to clarify a relationship between development of erosion and erosion intensity distribution by calculation, thereby allowing construction of a database.

As described above, for the erosion characteristics database according to this embodiment, the cavitation CFD is performed in consideration of the deformation of the structure due to erosion, thereby allowing construction of a database on erosion characteristics close to those of actual erosion.

The erosion characteristics database described above is an example of databases for performing an erosion prediction method described below, and not always essential. Specifically, other databases may be used for performing the erosion prediction method described below as long as they can define a relationship between a material and erosion.

Figure 4:
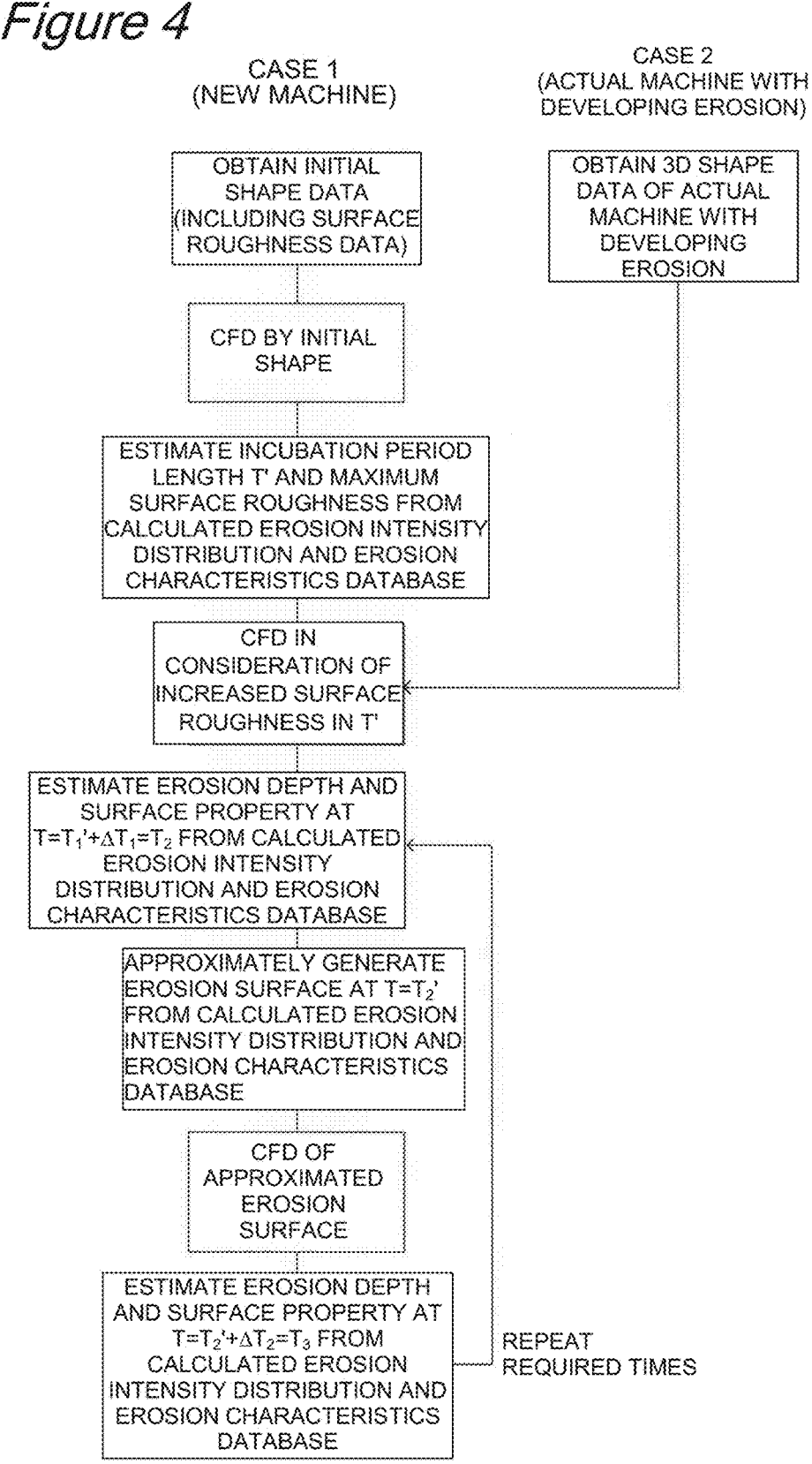
FIG. 4 is a flowchart of an erosion prediction process.

Next, a method for actually predicting erosion using the erosion characteristics database will be described in turn. FIG. 4 is a schematic flowchart of erosion prediction. FIG. 4 shows both a case with a new fluid machine (case 1), and a case with an already used fluid machine with developing erosion (case 2).

[Calculation of Cavitation Erosion Intensity Distribution]

[Obtaining Initial Shape Data]

First, to perform the cavitation CFD, initial shape data of a fluid machine to be predicted needs to be obtained. CAD data, if present, can be directly used for an initial shape of the fluid machine. If there is no CAD data, a shape of an actual fluid machine to be predicted is measured and obtained. As an example of a specific method for measuring an actual shape, three-dimensional data is reconstructed from superficial measurement using a laser light. The laser light is applied to a surface of the fluid machine to be predicted, and the reflected laser light is taken by a camera and converted into three-dimensional shape data.

[Grid Generation]

Next, to perform the CFD, a grid is generated with respect to a flow path formed in the fluid machine or the like. The grid generation is performed by calculating a shape of the flow path from shape data of the fluid machine, and defining each portion as an aggregate of grids from the calculated shape of the flow path. In the grid generation, grids near the surface of the fluid machine are formed to have a small size, and grids in other areas are formed to have a large size, thereby reducing time required for calculation while improving or maintaining calculation accuracy.

[Determination of Material]

Next, a material for forming the fluid machine is determined. This is because erosion characteristics differ depending on materials.

[Determination of Operation Condition]

Next, an operation condition for predicting erosion is determined. This is because the speed and amount of erosion produced in the fluid machine are influenced by the operation condition. For example, an operation time, an operation speed (for example, the number of rotations for a rotor), characteristics of a flowing fluid (for example, flow velocity, pressure, temperature, specific gravity, viscosity, or the like) are herein determined.

[Calculation of Cavitation Intensity Distribution]

For each grid, a numerical analysis of an initial shape is performed by CFD based on the operation condition to calculate cavitation intensity distribution in each portion. The cavitation intensity distribution is proposed by many researchers, and any calculation method may be used. A method having a high correlation with an experimental result is preferably selected in a stage of database creation. As an example, a method in Literature A ("Suuchi Kaiseki ni yoru Kyabiteshon Kaishoku Yosoku Gijutsu no Kaihatsu (Development of Cavitation Erosion Prediction Technique by Numerical Analysis)", by Nohmi Ikohagi, Iga, Papers of 59th lecture by Turbomachinery Society of Japan, (2008), pp. 49-54) is mentioned below. Local erosion intensity in a fluid is denoted by $c_a$, local pressure; p, local bubble amount; α (void fraction as bubble volume fraction); level of local pressure increase; Dp/Dt, and level of local bubble collapse; −Dα/Dt, then the following equation is obtained.

[Equation 1]

$$c_a = F\left(p, \alpha, \frac{Dp}{Dt}, -\frac{D\alpha}{Dt}\right) \quad (1)$$

When the influence of the erosion intensity propagates to any object surface, a time delay τ and attenuation $a_m$ of disturbance propagation occur. With a distance vector r from a point on the object to an attention point in a fluid area, instantaneous erosion intensity on the point on the object is defined as below.

[Equation 2]

$$C_{ao} = \int a_m(r) c_a(r, t-\tau) dV \quad (2)$$

For further simplification, a calculated value of a physical amount on the object surface without any time delay or attenuation is used as a representative. A flow velocity on the object surface is zero because of viscosity, and thus total differential in Equation (1) is replaced by partial differential. As functions F in Equation (1), the following simple four equations are exemplified.

[Equation 3]

$$F = \alpha \cdot \max\left[\frac{\partial p}{\partial t}, 0\right] \quad (3)$$

[Equation 4]

$$F = \alpha \cdot \max[(p - p_v), 0] \quad (4)$$

[Equation 5]

$$F = \max[(p - p_v), 0] \cdot \max\left[-\frac{\partial \alpha}{\partial t}, 0\right] \quad (5)$$

[Equation 6]

$$F = \max\left[-\frac{\partial \alpha}{\partial t}, 0\right] \quad (6)$$

Equations (3) to (6) define instantaneous values, while Equation (7) defines time average erosion intensity in consideration of cyclic changes of a cavitation flow.

[Equation 7]

$$\frac{1}{T_c}\int_0^{T_c} F \, dt \quad (7)$$

$T_c$ represents a representative cycle of a cavitation phenomenon in question. For example, $T_c$ is selected in accordance with a target such as a release cycle of cloud cavitation in a hydrofoil, a rotation cycle of a rotary machine, or a surging cycle if surging with cavitation occurs in a target system.

[Calculation of Erosion Intensity Distribution]

Erosion intensity distribution in each area of the fluid machine is calculated from the cavitation intensity distribution and the material used for the fluid machine or the like. Since the relationship between the material and the erosion intensity is constructed as the erosion characteristics database described above, this information is used for calculating the erosion intensity distribution.

[Change of Surface Roughness Condition and Recalculation of Cavitation Intensity Distribution by CFD]

[Estimation of Surface Roughness]

The change of surface roughness means virtually changing smoothness of a surface on the assumption that the shape of the fluid machine does not change. The surface of the fluid machine is subjected to a step referred to as an incubation period before development of erosion. The incubation period is a process in which erosion of the fluid machine has not been produced, but a recess or the like is formed in the surface to increase surface roughness. Using the erosion characteristics database described above allows prediction of the increase in surface roughness in the incubation period, and thus an estimated value of the surface roughness is also calculated for next erosion prediction. Estimated values on the surface roughness include an amount of increase in average surface roughness in the incubation period, an amount of increase in maximum surface roughness, the incubation period (time when the surface roughness increases), or the like.

[Recalculation of Cavitation Intensity Distribution]

Next, the estimated increase in surface roughness is reflected as a surface roughness effect of a fluid machine surface by CFD, as a boundary condition, to again perform cavitation CFD. Cavitation intensity distribution after the increase in surface roughness is recalculated by the CFD.

[Recalculation of Erosion Intensity Distribution]

The cavitation erosion intensity distribution recalculated in the above step is used to predict an erosion surface shape after a certain time from that time. The erosion characteristics database constructed by the method described above is also used for this prediction of the erosion surface shape. Information on the erosion surface shape includes, for example, an erosion depth or a surface property.

[Determination of Parameter on Representative Sphere]

[Determination of Radius Distribution of Representative Sphere]

To predict erosion, a shape change by one erosion is approximately expressed as cutting in a solid material portion by many spherical surfaces. Radius distribution of a representative sphere thereof is determined. Assumed radii of the representative sphere may be different or all the same.

[Determination of Center Position Distribution of Representative Sphere]

Next, to assume a position where erosion is produced, center position distribution of the representative sphere is determined. Center position distribution of the representative spheres is determined by erosion intensity distribution, and for example, for an area with high erosion intensity, a center position of many representative spheres is set. On the other hand, for an area with low erosion intensity, the number of representative spheres whose center position is set is small. Thus, in a position with higher erosion intensity, more representative spheres cause development of erosion.

[Determination of the Number of Deformations (the Number of Trials)]

Next, the number of deformations is determined. The number of deformations refers to the number of deformations caused by the representative spheres, and the larger number of deformations causes large deformation due to erosion by the representative spheres.

[Calculation of Approximate Erosion Surface]

Based on the initial shape data, the radius and center position distribution of the representative sphere, and the number of deformations caused by the representative sphere, the shape after erosion is calculated as an approximate erosion surface. Specifically, assuming that erosion caused by the representative sphere has developed from the initial shape, the shape after erosion is approximately expressed.

In this application, a method for mathematically approximating a combination of an indentation and a porous surface property in metal is proposed, and for other surface properties, a different mathematical method needs to be adopted. Also, it should be noted that the method for mathematically approximating a combination of an indentation and a porous surface property is not limited to the method suggested in this application. For example, as described in Literature B ("Riaristikku na Shizen Keikan Gazou no Tsuikyu (Pursuit of Realistic Natural Landscape Images)" by Nishida, 16th NIC COGRAPH/MULTIMEDIA paper contest, (2000), pp. 199-203), various techniques used for expressing natural objects in computer graphics fields, fractal theory, cellular automata, chaos, neuron, wavelet, genetic algorithm, L-system, or the like are applicable.

This application suggests two types of methods for calculating an approximate erosion surface.

The first calculation method simulates a situation in which "indentations are created, and surfaces of the indentations form a porous surface" found in an actual erosion surface, and includes the following:
1) A solid model without erosion is set.
2) A relatively smooth indentation (with a large radius of curvature) is provided in the solid model.
3) For the solid model with the relatively smooth indentations, an operation of hollowing the indentation surface and the solid model surface around the indentation surface is repeated multiple times using a spherical surface (having a smaller radius of curvature than the indentation) with a central coordinate located almost on the indentation surface.
4) A spherical surface previously hollowed in the hollowing operation is taken as a new surface, and the central coordinate of the sphere is located inside the surface of the original solid model.
5) The radius of the sphere and the number density of the spheres (the number of spheres per unit area) may have distribution. The distribution may locally change. This can provide a surface property such that only a bottom of the indentation has a fine porous surface.
6) In consideration of the distribution, the hollowing operation uses random numbers, and randomness of an actual erosion surface shape is also expressed.

In using the mathematical expressions as described above, the shape of "indentation" is defined by depth distribution from the solid model surface, and local radius distribution (a range between a maximum radius and a minimum radius, and an existence probability for each radius are provided) and local number density distribution of the spheres are provided to the surface including the "indentation". More simply, several types of representative sphere radii and number density for each type may be provided.

Figure 5:
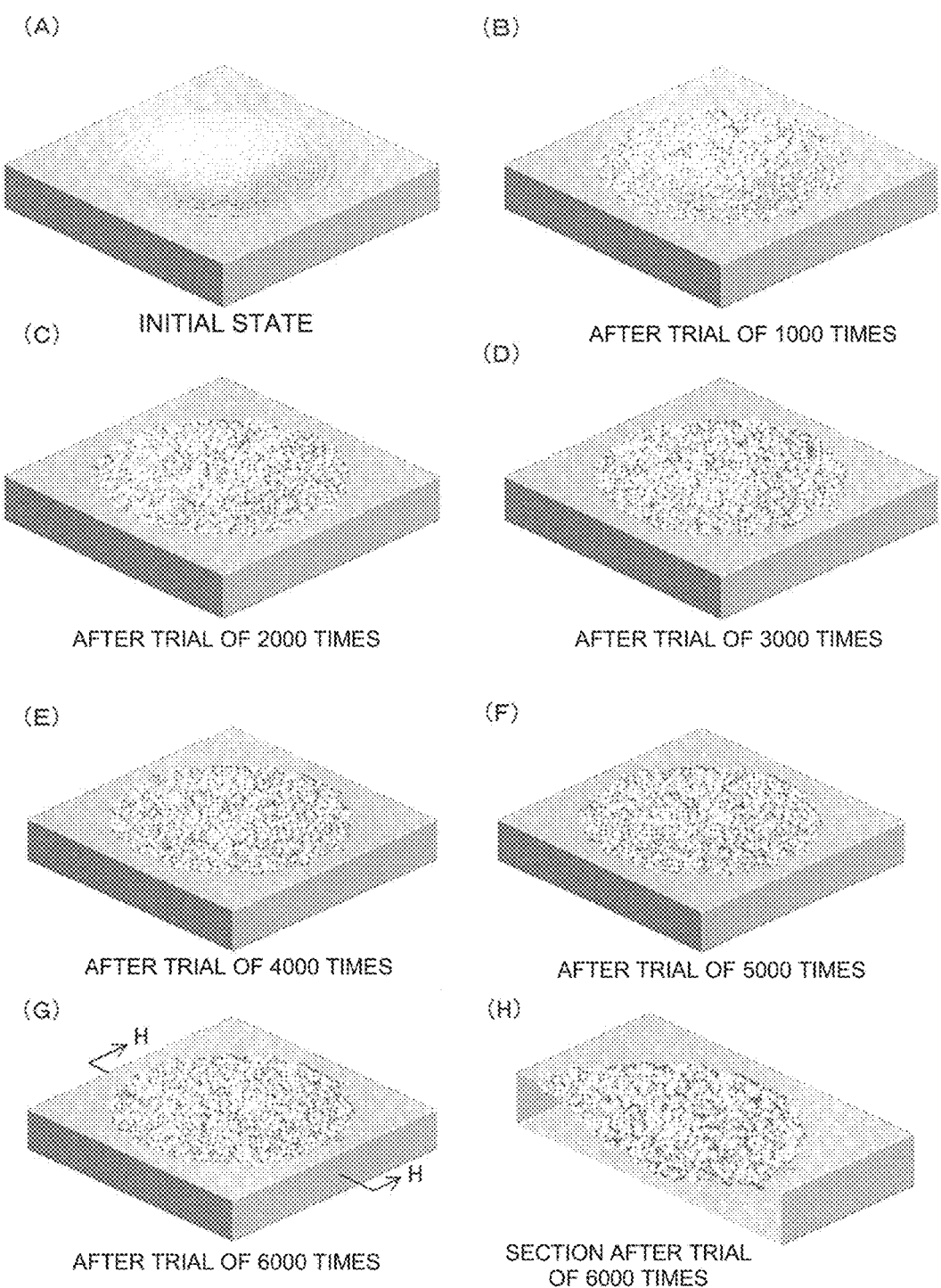
FIG. 5 illustrates changes in an approximate erosion surface using a representative sphere.

FIG. 5 illustrates changes in the number of trials and the approximate erosion surface based on the above described method, and shows a situation in which an initial indentation created by rotating a sine curve on a rectangular parallelepiped solid model is hollowed 6000 times by a sphere having the same radius. FIG. 5(A) is a perspective view showing an initial shape, including a partially spherical shape as an example. FIGS. 5(B) to 5(G) show states of an approximate erosion surface when the number of trials is increased in increments of 1000. Specifically, FIG. 5(B) shows the case with the number of trials of 1000, and FIG. 5(G) shows the case with the number of trials of 6000. FIG. 5(H) is a sectional view taken along the line H-H in FIG. 5(G).

Figure 7:
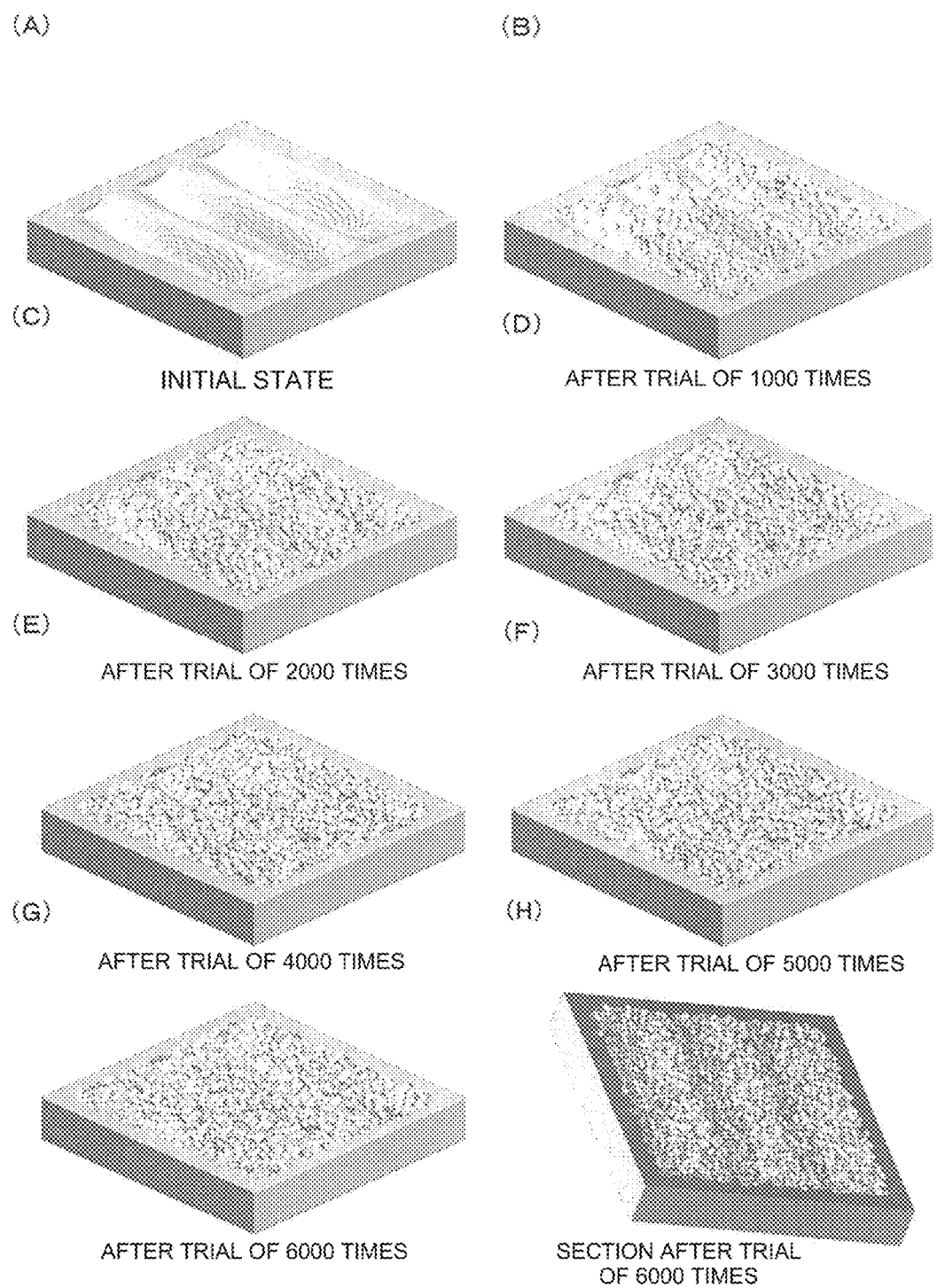
FIG. 7 illustrates changes in an approximate erosion surface using a representative sphere by creating an initial indentation having a plurality of grooves expressed in sine curves on a rectangular parallelepiped solid model.

FIG. 6 shows a situation in which an entire upper surface of a rectangular parallelepiped solid model including an initial indentation created by rotating a sine curve is hollowed 6000 times by a sphere having the same radius. FIG. 7 shows a situation in which an initial indentation having grooves expressed in sine curves is created on a rectangular parallelepiped solid model, and an indentation surface is hollowed 6000 times by a sphere having the same radius.

The second calculation method simulates a situation in which "indentations are created, and surfaces of the indentations form a porous surface" found in an actual erosion surface, and includes the following:
1) A solid model without erosion is set.
2) For the solid model, an operation of hollowing the solid model surface is repeated multiple times using a spherical surface with a central coordinate located almost on the surface (having a smaller radius of curvature than the indentation).
3) A spherical surface previously hollowed in the hollowing operation is taken as a new surface, and the central coordinate of the sphere is located inside the surface of the original solid model.
4) The radius of the sphere and the number density of the spheres (the number of spheres per unit area) may have distribution. The distribution may locally change. Thus, the area with high number density is deeply hollowed, and indentations are entirely formed. Also, this can provide a surface property such that only a bottom of the indentation has a fine porous surface.
5) In consideration of the distribution, the hollowing operation uses random numbers, and randomness of an actual erosion surface shape is also expressed.
6) In using such mathematical expressions, local radius distribution (a range between a maximum radius and a minimum radius, and an existence probability for each radius are provided), and local number density distribution of the spheres are provided to the solid model surface. More simply, several types of representative sphere radii and local number density for each type may be provided.

To approximately generate an erosion surface having certain depth distribution using this method, the hollowing operation may be repeated with number density distribution of the spheres similar to the depth distribution, and finished when indentations almost identical to the depth distribution are formed.

Figure 8:
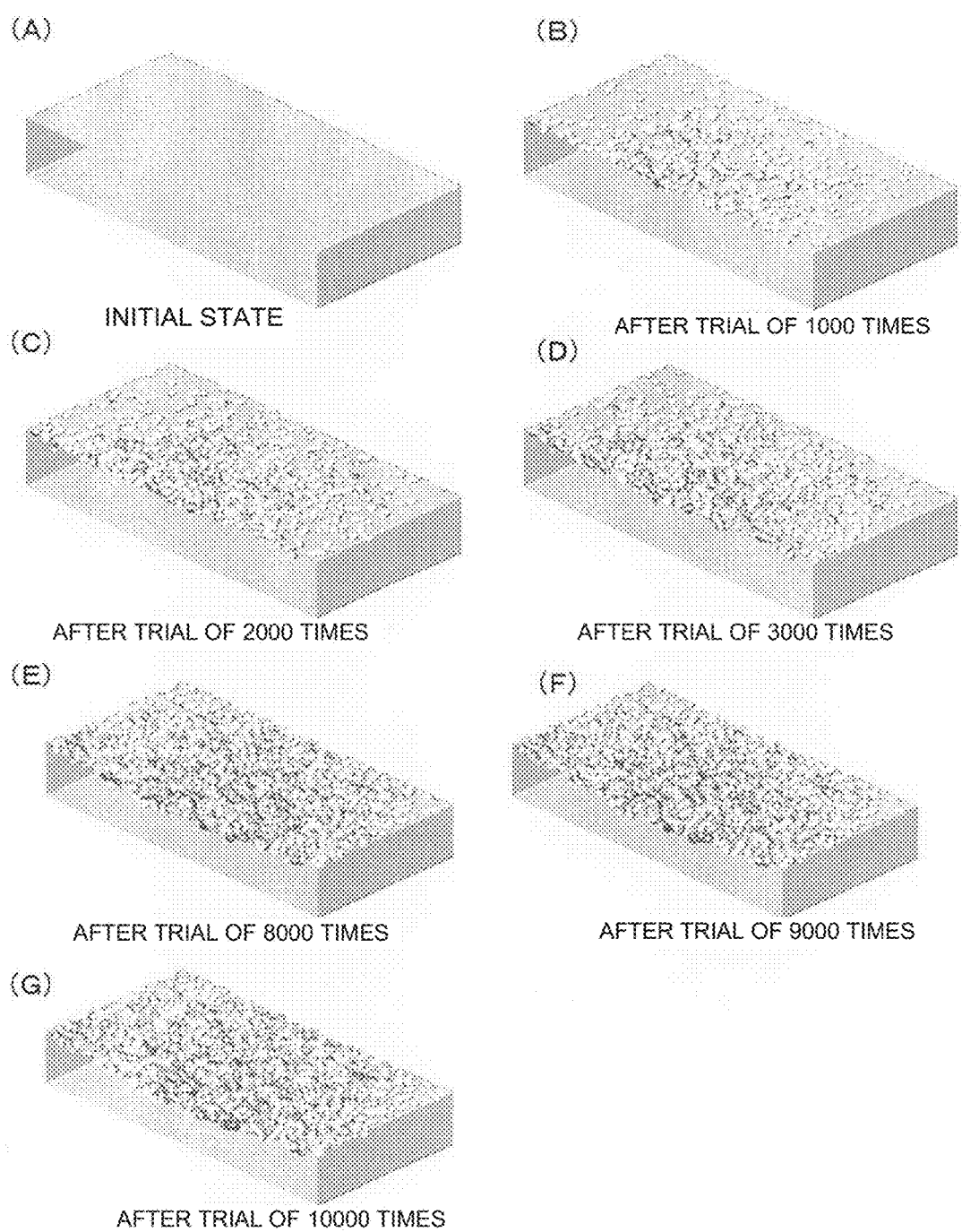
FIG. 8 is a sectional view cut along a middle showing a situation in which the upper surface of the rectangular parallelepiped solid model is hollowed 10000 times by a sphere having the same radius.

FIG. 8 shows a situation in which an upper surface of a rectangular parallelepiped solid model is hollowed 10000 times by a sphere having the same radius, providing normal distribution with a constant sphere radius and the number density of the spheres being maximum in the center position of the upper surface of the solid model. FIG. 8 shows states cut along a middle.

If the erosion speed for each type of the material in the local solid material is accurately associated with the local erosion intensity by computational fluid dynamics (CFD) using a theoretical formula or an empirical formula, the analysis on the fluid side and the erosion analysis on the material side are simultaneously coupled for a numeral analysis, thereby allowing an erosion surface to be predicted without using the approximate erosion surface as suggested in this application. As an example, FIG. 9 shows results of damage to a fluid machine surface due to sand particles mixed into a fluid, which is a similar phenomenon in this technical field, being obtained by a coupled analysis of the fluid side and the material side. It can be seen from FIG. 9 that a relatively smooth indentation can be predicted. Literature C ("Ryutai Kikai ni okeru sando erojon genshou no Suuchi Yosoku (Prediction of Numerical Value of Sand Erosion Phenomenon in Fluid Machine)" by Yamamoto and Suzuki, Nagare (Flow), 27, (2008), pp. 127-132).

However, in the cavitation erosion field, an erosion process in a minute scale has not been sufficiently clarified, and the theoretical formula or the empirical formula cannot be easily obtained. The actually observed cavitation erosion surface shows, for example, a porous extremely complex shape. Thus, even if the theoretical formula or the empirical formula is obtained, to precisely define the complex shape, an extremely large number of calculation grids must be used to express the shape on both the fluid side and the material side. Thus, calculation unrealistically takes enormous time. Thus, in a range of current computer capacity, the method of this application of mathematically approximating the surface subjected to cavitation erosion, associating parameters for the approximation (local average depth or numerical information on a representative sphere group) with cavitation erosion intensity by CFD, and databasing the association is effective and realistic.

[Calculation of Cavitation Intensity Distribution by CFD for Shape after Deformation]

Based on the approximate erosion surface expressing the shape after deformation, a grid is regenerated for a flow path, cavitation intensity distribution by CFD is calculated, then returning to the process of calculating the erosion intensity distribution, and erosion intensity distribution is recalculated based on obtained new cavitation intensity distribution. An erosion surface shape after a lapse of a certain time from that time is predicted.

For grid generation near the approximate erosion surface, a general grid formation method may be used. However, since grid generation is complex due to the complex shape of the erosion surface, the erosion surface may be easily expressed as a cubic or rectangular parallelepiped voxel and by presence or absence of a voxel. Also, a method of handling a free surface or a complex surface shape such as a level set method, a VOF method, or a boundary embedding method may be used.

By each of the above processes, the erosion intensity change in consideration of the deformation due to erosion can be considered, thereby allowing prediction of erosion closer to actual erosion. Also, repeating the process of calculating the erosion intensity distribution, approximating the erosion surface, and then recalculating the erosion intensity distribution allows accurate prediction of erosion development due to long-term use.

The erosion prediction for the new fluid machine has been described above. However, the present invention is not limited to this. Specifically, the present invention is applicable to an actual fluid machine with already developing erosion. Specifically, as shown in the case 2 in FIG. 3, shape data of a fluid machine with developing erosion is obtained, cavitation CFD of the shape with erosion is performed, and the above described method is used to predict development of erosion thereafter. In this embodiment, the incubation period described above has been already finished, and thus the process of calculating the erosion intensity distribution, approximating the erosion surface, and then recalculating the erosion intensity distribution may be simply repeated. The shape with erosion is measured using a 3D laser measuring machine or an impression material. 3D laser measurement cannot be applied to a portion with a so-called octopus pot shape with a broader deep portion than an opening of a hole due to erosion. However, this can be complemented using a soft impression material (molding material), or a technique of an X-ray imaging device or a CT scanner.

The erosion prediction method described above can be achieved as an erosion prediction system. The erosion prediction system includes a computer and an erosion prediction program. Specifically, a storage device of the computer stores the erosion characteristics database and the erosion prediction program described above.

In erosion prediction, the shape data of the fluid machine is first input to the computer via input means. The shape data is CAD data or actually measured data of the fluid machine. Further, information on the material that forms the fluid machine is further input from the input means. Then, an erosion prediction period is input. For the erosion prediction period, a period for which the fluid machine is predicted to be damaged by erosion is set, for example, one year, five years, or ten years.

A CPU of the computer refers to information in the erosion property database based on the input shape data and information on the material to calculate the shape change of the fluid machine due to erosion. Then, the calculation result is displayed on display means connected to the computer. At this time, based on the shape prediction due to erosion over time, for example, shape changes over 10 years are desirably displayed by animation of about several seconds.

Allowing the erosion prediction described above achieves enlargement of application ranges as described below. Specifically, the present invention can be applied to a design method of the fluid machine based on the erosion prediction. Specifically, based on the result of the erosion prediction, an initial shape of the fluid machine is designed in consideration of erosion prediction such that a portion where erosion easily develops is set to be thick, thereby allowing flexible setting of useful life.

Also, the present invention can be applied to a maintenance method based on the erosion prediction. Specifically, if erosion prediction is possible, the shape of the erosion surface of the actually used fluid machine is compared with a predicted shape, and the life of the fluid machine can be predicted based on the result of the comparison. This allows prediction of timing of required maintenance. Further, erosion prediction under various operation conditions can be performed to allow calculation of an operation condition for preventing erosion of the fluid machine.

INDUSTRIAL APPLICABILITY

The present invention can be applied to prediction of erosion characteristics of a fluid machine.

The invention claimed is:
1. A method for predicting erosion of a fluid machine produced due to cavitation, the method comprising:
conducting a cavitation test on a test piece;
measuring erosion on the test piece caused by the cavitation test;
calculating erosion intensity generated on the test piece during the cavitation test using cavitation Computational Fluid Dynamics (CFD);
creating an erosion characteristics database containing information relating to the erosion obtained from the cavitation test and calculated erosion intensity;
calculating erosion intensity distribution in each area of the fluid machine from cavitation flow field characteristics obtained using the cavitation CFD for a flow path formed by the fluid machine;

calculating a surface after erosion of the fluid machine as an approximate erosion surface based on the erosion intensity distribution and the database;

recalculating erosion intensity distribution in each area of the fluid machine using the cavitation CFD for a flow path including the calculated approximate erosion surface; and calculating a shape after deformation of the approximate erosion surface based on the recalculated erosion intensity distribution and the database, wherein calculating the approximate erosion surface includes:

determining radius distribution and center position distribution of a representative sphere and the number of shape deformations by the representative sphere for assuming an erosion surface having a porous surface property based on the erosion intensity distribution; and calculating a shape after deformation of the approximate erosion surface based on the determined information on the representative sphere.

2. The erosion prediction method according to claim 1, further comprising: calculating erosion depth distribution produced in the fluid machine surface based on the erosion intensity distribution; and calculating the shape after deformation of the approximate erosion surface also using the erosion depth distribution.

3. The erosion prediction method according to claim 1, comprising: prior to the calculation of the erosion intensity distribution, calculating the erosion intensity distribution in each area for an initial shape of the fluid machine without erosion from the cavitation flow field characteristics obtained using the cavitation CFD;

changing surface roughness in each area of the fluid machine surface for assuming minute deformation action in a latent period in an early stage of erosion based on the erosion intensity distribution;

calculating erosion intensity distribution for the initial shape again by the cavitation CFD; and predicting erosion based on the calculated erosion intensity distribution.

4. The erosion prediction method according to claim 1, comprising: prior to the calculation of the erosion intensity distribution, measuring the shape of the fluid machine in which erosion has been already produced by an actual operation;

calculating, based on the measurement result, erosion intensity distribution for the shape including erosion of the fluid machine using the cavitation CFD for a flow path including the erosion surface that has been already produced; and predicting erosion based on the calculated erosion intensity distribution.

5. An erosion prediction system for performing an erosion prediction method according to claim 1, the erosion prediction system comprising:

a computer having a storage and a central processing unit (CPU);

an input for inputting information in the computer; and a display for displaying a result calculated by the computer, wherein the storage stores an erosion prediction program for performing the erosion prediction method, the CPU reads the erosion prediction program from the storage, calculates a predicted shape of a fluid machine after erosion based on shape data and material information of the fluid machine input by the input, and displays information on the predicted shape on the display.

6. The erosion prediction system according to claim 5, wherein the CPU calculates a shape change of the fluid machine over time, and displays the shape change on the display by animation.

7. The erosion prediction system according to claim 5, wherein the storage stores information in an erosion characteristics database, and the information in the database is used for erosion prediction, the database comprising information on material names, material properties, and erosion characteristics for predetermined erosion intensity, wherein the erosion characteristics include an erosion volume, an erosion depth, erosion depth distribution, and a surface property of an erosion surface, and the surface property is surface roughness or a surface shape pattern of the fluid machine.

8. The erosion prediction method according to claim 1, wherein the database comprising information on material names, material properties, and erosion characteristics for predetermined erosion intensity, wherein the erosion characteristics include an erosion volume, an erosion depth, erosion depth distribution, and a surface property of an erosion surface, and the surface property is surface roughness or a surface shape pattern of the fluid machine.

9. A non-transitory computer-readable storage medium storing an erosion prediction program that is executable by a computer for preforming an erosion prediction method according to claim 1.

10. The erosion prediction method according to claim 1, wherein the cavitation test is conducted using a cavitation jet or a Venturi tube.

11. The erosion prediction method according to claim 1, wherein the erosion on the test piece caused by the cavitation test is measured by a 3D laser scanner or an impression material.

12. An erosion prediction system for predicting erosion of a fluid machine produced due to cavitation, the method comprising:

means for conducting a cavitation test on a test piece;

means for measuring erosion on the test piece caused by the cavitation test;

means for calculating erosion intensity generated on the test piece during the cavitation test using cavitation Computational Fluid Dynamics (CFD);

means for creating an erosion characteristics database containing information relating to the erosion obtained from the cavitation test and calculated erosion intensity;

means for calculating erosion intensity distribution in each area of the fluid machine from cavitation flow field characteristics obtained using the cavitation CFD for a flow path formed by the fluid machine;

means for calculating a surface after erosion of the fluid machine as an approximate erosion surface based on the erosion intensity distribution and the database;

means for recalculating erosion intensity distribution in each area of the fluid machine using the cavitation CFD for a flow path including the calculated approximate erosion surface; and means for calculating a shape after deformation of the approximate erosion surface based on the recalculated erosion intensity distribution and the database.

13. The erosion prediction system according to claim 12, wherein the means for calculating the surface after erosion of the fluid machine as the approximate erosion surface includes:

means for determining radius distribution and center position distribution of a representative sphere and the number of shape deformations by the representative sphere for assuming an erosion surface having a porous surface property based on the erosion intensity distribution; and means for calculating a shape after deformation of the approximate erosion surface based on the determined information on the representative sphere.

14. A method for predicting erosion of a fluid machine produced due to cavitation, the method comprising:

calculating erosion intensity distribution in each area of the fluid machine from cavitation flow field characteristics obtained using cavitation computational fluid dynamics (CFD) for a flow path formed by the fluid machine;

calculating a surface after erosion of the fluid machine as an approximate erosion surface based on the erosion intensity distribution;

recalculating erosion intensity distribution in each area of the fluid machine using the cavitation CFD for a flow path including the calculated approximate erosion surface; and calculating a shape after deformation of the approximate erosion surface based on the recalculated erosion intensity distribution, wherein the calculating the approximate erosion surface includes:

determining radius distribution and center position distribution of a representative sphere and the number of shape deformations by the representative sphere for assuming an erosion surface having a porous surface property based on the erosion intensity distribution; and calculating a shape after deformation of the approximate erosion surface based on the determined information on the representative sphere.

* * * * *